United States Patent [19]
Fercher

[11] Patent Number: 6,124,930
[45] Date of Patent: Sep. 26, 2000

[54] METHOD AND ARRANGEMENT FOR TRANSVERSE OPTICAL COHERENCE TOMOGRAPHY

[75] Inventor: Adolf Friedrich Fercher, Vienna, Austria

[73] Assignee: Carl Zeiss Jena GmbH, Jena, Germany

[21] Appl. No.: 09/118,634

[22] Filed: Jul. 17, 1998

[30] Foreign Application Priority Data

Jul. 21, 1997 [AT] Austria ................................... 1235/97

[51] Int. Cl.[7] .................................................. G01B 9/02
[52] U.S. Cl. ........................ 356/359; 356/345; 356/357
[58] Field of Search .................................. 356/359, 351, 356/345, 357, 358

[56] References Cited

U.S. PATENT DOCUMENTS

| | | | |
|---|---|---|---|
| 5,321,501 | 6/1994 | Swanson et al. | 356/345 |
| 5,847,827 | 12/1998 | Fercher | 356/345 |
| 5,973,781 | 10/1999 | Moeller et al. | 356/345 |
| 6,057,920 | 5/2000 | Fercher et al. | 356/357 |

*Primary Examiner*—Robert H. Kim
*Assistant Examiner*—Andrew H. Lee
*Attorney, Agent, or Firm*—Reed Smith Shaw & McClay LLP

[57] ABSTRACT

Figure 2:
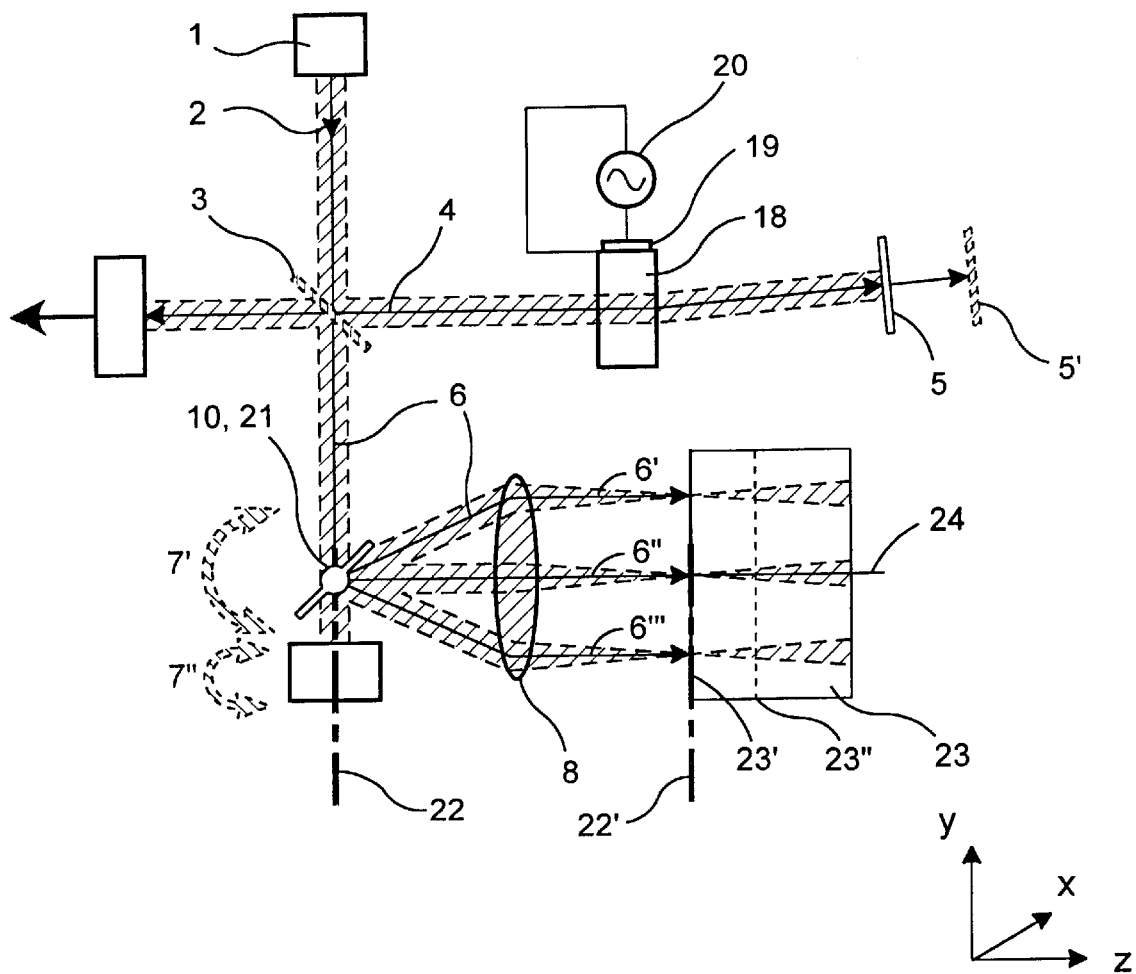

A problem occurring in the acquisition of planar sectional images by means of transverse optical coherence tomography consists in that the frequency of the photoelectric interferometer signal is not constant during the scanning process. The corresponding frequency bandwidth impedes the electronic bandpass filtering required for noise reduction. However, planar tomographic images are particularly important. A beam path which is telecentric on the object side is realized in that the center of rotation of the pair of scanning mirrors which directs the scanning measurement beam onto the object is arranged in the focal plane of the focussing optics. In this way, the frequency of the photoelectric interferometer signal remains constant during the scanning of planar object sections, which enables optimum noise filtering. The invention is best represented by FIG. 2.

6 Claims, 3 Drawing Sheets

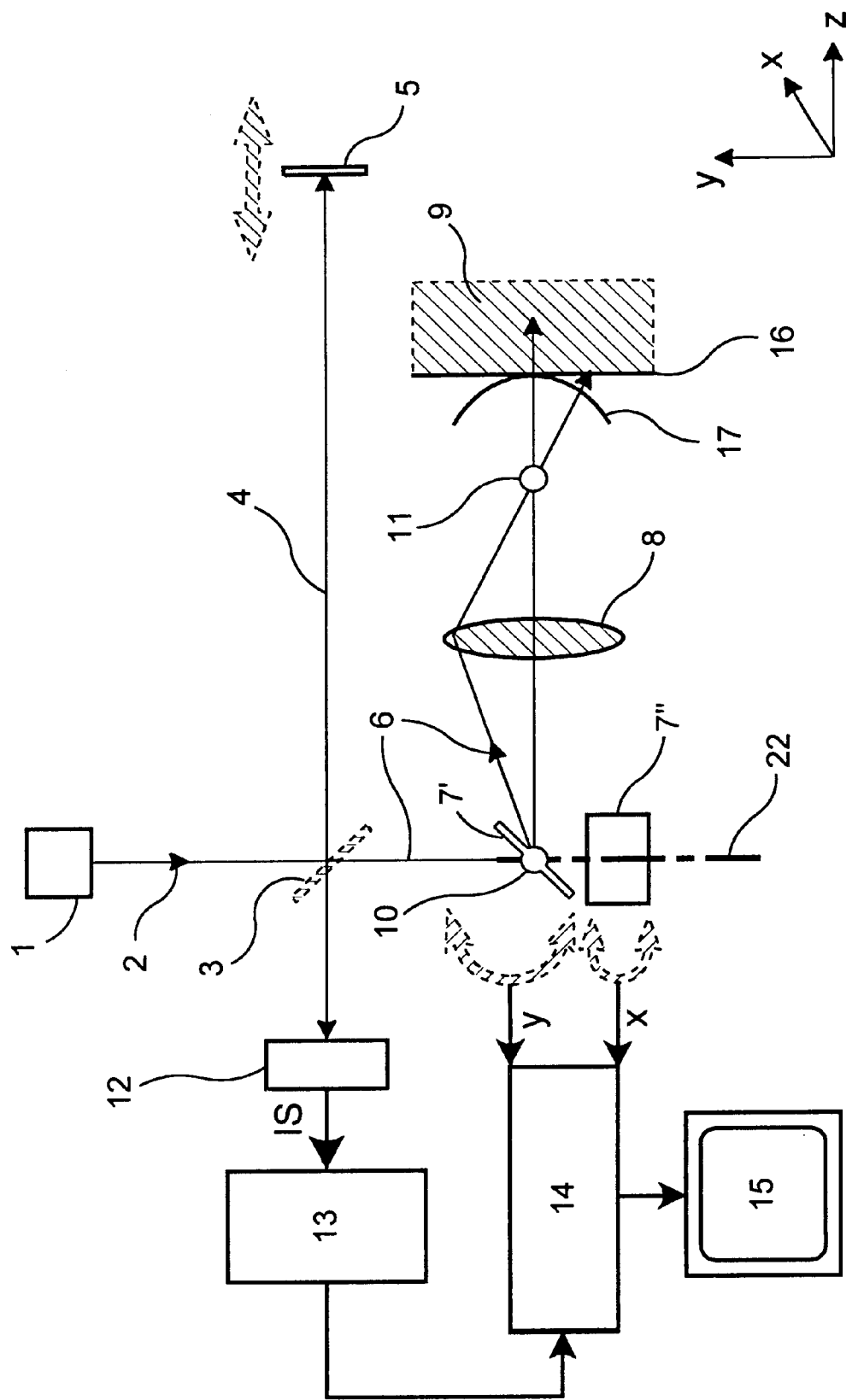
F I G. 1

METHOD AND ARRANGEMENT FOR TRANSVERSE OPTICAL COHERENCE TOMOGRAPHY

This invention is directed to the field of optical image acquisition in medicine.

Prior Art: In transverse optical coherence tomography, a transverse sectional image of an object is acquired in that the measurement beam of a shortcoherencee interferometer is scanned over the surface of the object so as to comprehend surface area, that is, for example, in an S-shaped or wavy manner. This scanning movement gives the x- and y-coordinates of the image. In every x-y position, the measurement beam also penetrates into the object in the z-direction. The depth position $z_0$ from which the diffusely reflected light is recorded is determined by means of the tomographic short-coherence interferometer. In this way, a tomographic image $I(x,y,z_0)$ of the object is obtained in the transverse direction, i.e., in the direction normal to the scanning light beam.

Transverse optical coherence tomography of the type mentioned above was first described by A. Gh. Podoleanu, G. M. Dobre, D. J. Webb, and D. A. Jackson in Optics Letters, Volume 21, 1996, pages 1789 to 1791. The process described by these authors is presented in a simplified manner in FIG. 1.

The letters and numbers in these and the following Figures are:

1 light source with short temporal coherence
2 spatially coherent light beam with short temporal coherence
3 splitter mirror
4 reference beam
5 reference mirror
6 measurement beam
7' and 7" pair of scanning mirrors with axes of rotation extending normal to one another
8 focussing optics
9 object from which the tomographs are prepared
10 center of rotation of the pair of scanning mirrors 7' and 7"
11 image of center of rotation 10
12 photodetector
13 electronics for amplification and bandpass filtering of the interferometer signal
14 computer
15 monitor
16 planar object surface
17 spherical surface
18 fused silica block
19 transducer
20 AC voltage source
21 focal point of focussing optics
22 focal plane of focussing optics
23 object
23' and 23" section planes of tomographic imaging
24 optical axis of zoom optics
25 zoom optics
26 optical axis of focussing optics
27 and 27' section planes of tomographic imaging inclined relative to optical axis In FIG. 1, the light source 1, for example, a superluminescent diode, emits a spatially coherent light beam 2 with short temporal coherence. This light beam strikes the splitter mirror 3 of a modified Michelson interferometer. The splitter mirror 3 reflects a partial beam 4 as a reference beam to the reference mirror 5. The partial beam 6 penetrating the splitter mirror 3 forms the measurement beam. This measurement beam is directed onto the object 9 by the pair of scanning mirrors 7' and 7" with axes of rotation normal to one another via optics 8 and scans this object 9 in the x- and y-direction. It can be assumed by approximation that the pair of scanning mirrors 7' and 7" deflects the measurement beam 3 proceeding from a common center of rotation 10. The optics 8 form the center of rotation 10 of the pair of scanning mirrors 7' and 7" in point 11. All of the measurement beams 6 scanning the object 9 pass through this point. The light bundles diffusely reflected by the object 9 and reflected by the reference mirror 5 reach the photodetector 12 via the scanning mirrors 7' and 7" and via the splitter mirror 3 and interfere at the photodetector 12. The occurring photoelectric interferometer output signal IS is utilized as an image signal $I(z,y,z_0)$ after amplification and bandpass filtration in subsequent electronics 13 for noise reduction. A computer 14 records the magnitude of the photoelectric interferometer output signal IS and the respective x-and y-positions with reference to the signals from the scanning mirrors 7' and 7". The image that is prepared in this way is displayed by the computer on a monitor 15 or is read out in some other way.

When a planar object surface 16 is imaged by the arrangement according to FIG. 1, the path length of the measurement beam 6 changes. This path length would be constant with respect to the spherical surface 17 (with center 11), but not with respect to the planar surface 16. Since the optical path length in the measurement beam obviously changes during the process of scanning a planar surface, alternately constructive and destructive interferences occur at the photodetector. The interferometer output signal IS accordingly undergoes a frequency modulation. The frequency bandwidth which is accordingly generated in the interferometer signal impedes electronic bandpass filtering. The authors mentioned above therefore state in the last paragraph of the above-cited article that by shifting the measurement beam out of the center of rotation of the scanning mirror the interferometer signal can be given a higher fundamental frequency and the relative frequency bandwidth can accordingly be reduced. However, this does not entirely solve the problem of the frequency bandwidth; further, an asymmetrical beam path results with corresponding imaging errors and distorted image surfaces. However, for obvious reasons, planar tomographic images are particularly important.

The invention therefore provides a process and arrangements in which:

1. planar object surfaces can be scanned without changes in the optical path length in the measurement beam, and
2. the frequency of the photoelectric interferometer output signal IS remains constant, which enables optimum noise filtering.

A first arrangement of the process according to the invention is shown in FIG. 2. In this case also, the light source 1, for example, a superluminescent diode, emits a spatially coherent, parallel light beam 2 with short temporal coherence. This light beam strikes the splitter mirror 3 of a Michelson interferometer which is modified as a short-coherence interferometer. The splitter mirror 3 splits the light beam bundle 2 into a measurement beam 6 and reference beam 4.

The reference beam 4 is reflected to the reference mirror 5 and, in so doing, passes through an acousto-optic frequency modulator, for example. Acoustooptic frequency modulators are known from the prior art. They are formed, for example, of a transparent fused silica block 18 connected to a transducer 19. The transducer is operated by an AC voltage source 20. The sound waves traveling through the fused silica block 18 generate therein a Bragg diffraction grating which moves at the speed of sound. The reference beam 4 is diffracted at this grating when passing back and forth and, in this way, simultaneously undergoes a Doppler shift of the light frequency by an amount $\Delta v$. Other, e.g., electrooptical, methods for the frequency shifting of the reference light bundle in accordance with the prior art can also be used. Further, the device for frequency shifting can also be arranged in the measurement beam 6 instead of in the reference beam 4.

The measurement beam 6 first strikes the pair of scanning mirrors 7' and 7" whose axes of rotation extend normal to one another. The common center of rotation 10 of the pair of scanning mirrors 7' and 7" is arranged, according to the invention, in the focal plane 22 of the focussing optics 8, for example, in the focal point 21. This gives a beam path which is telecentric on the object side. The parallel measurement beam bundle 6 is now focussed by the focussing optics 8 in the object-side focal plane 22', which is indicated in FIG. 2 by three beam positions 6', 6" and 6'" located one after the other with respect to time. In this case, all optical lengths from the focal point 21 to the object-side focal plane 22' are equal. Therefore, when a planar surface—in this case, the focal plane 22'—is scanned, there is no change in the optical path length in the measurement beam 6 and also no additional frequency modulation of the interferometer signal. In the arrangement according to FIG. 2, the surface 23' of the object 23 lies in the focal plane 22'. A planar area is now scanned at the surface 23' by means of the pair of scanning mirrors 7' and 7".

The frequency-shifted reference light interferes at the interferometer output with the measurement light diffusely reflected by the object. The resulting intensity oscillates at frequency $\Delta v$, which enables bandpass filtering. In this respect, it must still be taken into account that, because of the use of a light source with low temporal coherence, only those light components from the reference beam and measurement beam which have traveled the same optical path lengths within the coherence length are capable of interference. Therefore, the optical path length from the beam splitter 3 to the plane 23' to be imaged and back to the beam splitter 3 must be equal to the optical path length from the beam splitter 3 to the reference mirror 5 and back to the beam splitter 3. The position of the reference mirror 5 in the reference beam path accordingly determines the z-position of the plane 23' which is imaged. In order to image other object planes, either the object 23 is shifted in the beam direction or the reference mirror 5 is shifted, for example, into position 5'. The object plane 23" is now imaged.

Figure 3:
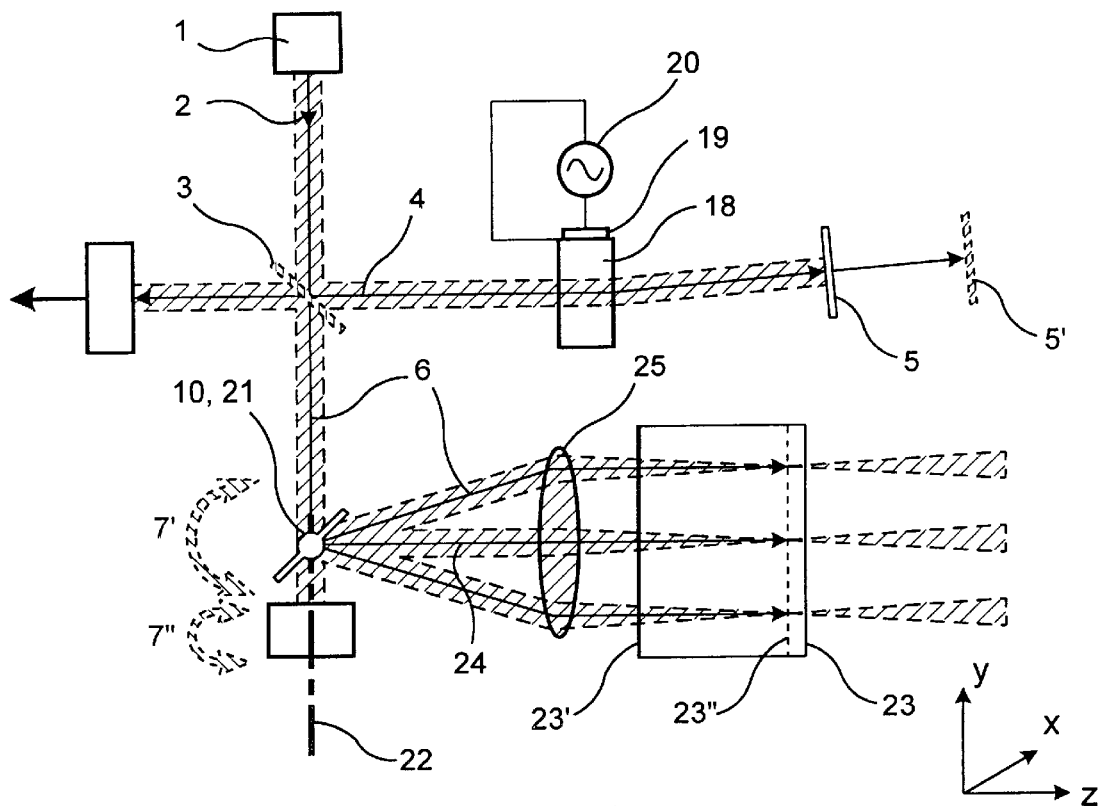

If only the reference mirror 5 is shifted in order to image other object planes, for example, plane 23', the transverse resolution is worsened because the measurement light beam is not focussed in plane 23", but rather in plane 23'. In order to overcome this disadvantage, the focussing optics 8 can be constructed as zoom optics 25. When the focal length of the zoom optics 25 is changed—the focus 21 remaining the same—planar transverse tomograms with high resolution can be acquired from different object planes without displacing the object. This is shown in FIG. 3. Compared with the arrangement according to FIG. 2, the zoom optics 25 in the example shown in FIG. 3 have a greater focal length than the focussing optics 8. Accordingly, a plane 23" lying deeper in the object 23 is imaged. Naturally, the reference mirror 5 must at the same time be displaced into the corresponding position 5" to adapt to the path lengths in the reference beam and measurement beam.

Figure 4:
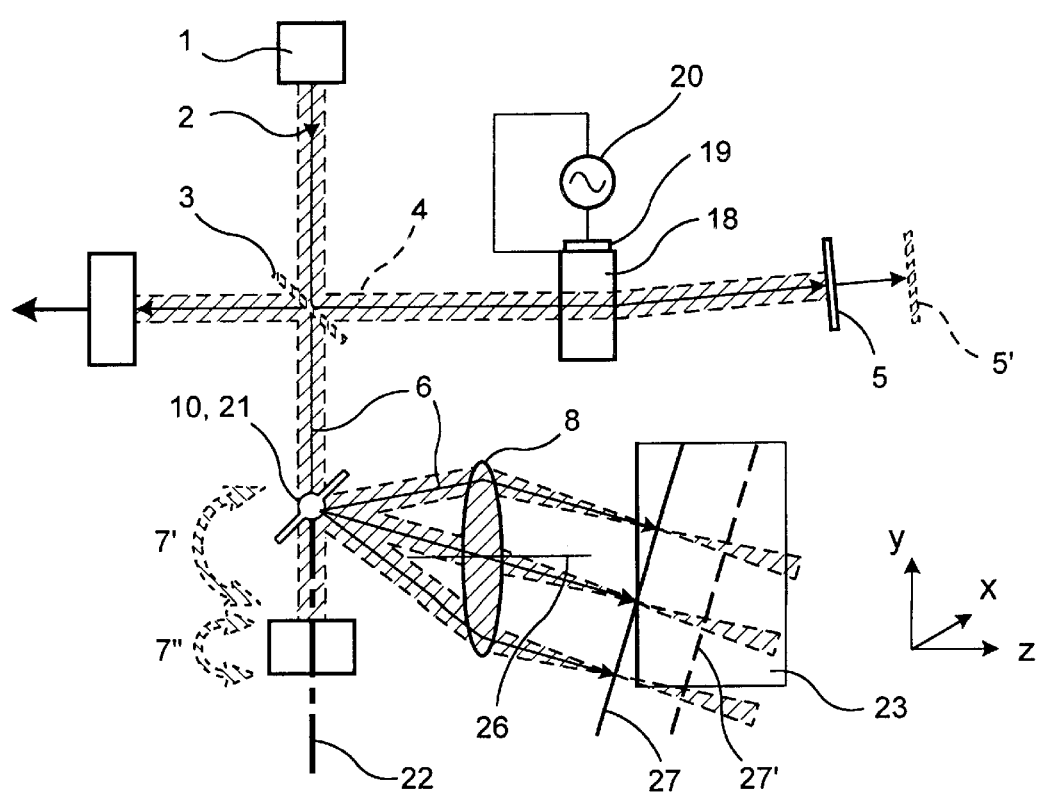

By means of further modification, transverse tomographs can also be acquired at any desired angles. This is shown in the arrangement according to FIG. 4. When the center of rotation 10 of the pair of scanning mirrors 7' and 7" is moved out of the optical axis 26 of the focussing optics 8 and accordingly remains in the focal plane 22, correspondingly inclined section planes 27 or 27' are imaged.

What is claimed is:

1. Apparatus for performing transverse planar optical short-coherence tomography, comprising:

source means for supplying a light source with short temporal coherence;

an interferometer for splitting the light source into a measurement beam and a reference beam;

focussing optics for focussing a scanning measurement beam onto an object to be scanned; and rotatable scanning mirrors for directing the measurement beam onto the focussing optics to produce the scanning measurement beam, said scanning mirrors being disposed within a focal point of said focussing optics, said focussing optics supplying the scanning measurement beam along a scanning beam path that extends in a telecentric manner to achieve planar tomographic imaging of the object without additional frequency modulation of the output of the interferometer.

2. The apparatus of claim 1, further comprising an acousto-optic frequency modulator and a reference mirror, said reference beam output from the interferometer passing through the acousto-optic frequency modulator before striking the reference mirror, said reference beam undergoing a Doppler shift as a result of passing through the acousto-optic frequency modulator.

3. The apparatus of claim 1, wherein said rotatable scanning mirrors includes first and second scanning mirrors whose axes of rotation are normal to one another, and a center of rotation of each of said first and second scanning mirrors being in the focal point of the focussing optics to provide the scanning beam path produced by the focussing optics that extends in the telecentric manner.

4. Apparatus for performing transverse planar optical short-coherence tomography, comprising:

source means for supplying a light source with short temporal coherence;

an interferometer for splitting the light source into a measurement beam and a reference beam;

zoom optics for focussing a scanning measurement beam within an object to be scanned so that a plane lying within the object is imaged; and rotatable scanning mirrors for directing the measurement beam onto the zoom optics to produce the scanning measurement beam, said scanning mirrors being disposed within a focal point of said zoom optics, said zoom optics supplying the scanning measurement beam along a scanning beam path that extends in a telecentric manner to achieve planar tomographic imaging of the plane lying within the object without additional frequency modulation of the output of the interferometer.

5. Apparatus for performing transverse planar optical short-coherence tomography, comprising:

source means for supplying a light source with short temporal coherence;

an interferometer for splitting the light source into a measurement beam and a reference beam;

focussing optics for focussing a scanning measurement beam onto or within an object to be scanned; and rotatable scanning mirrors for directing the measurement beam onto the focussing optics to produce the scanning measurement beam, said scanning mirrors being disposed within a focal plane of said focussing optics, but not being disposed on an optical axis of said focussing optics, said focussing optics supplying the scanning measurement beam along a scanning beam path that extends in a telecentric manner to achieve planar tomographic imaging of an inclined section plane of the object without additional frequency modulation of the output of the interferometer.

6. The apparatus of claim 5, wherein said rotatable scanning mirrors includes first and second scanning mirrors whose axes of rotation are normal to one another, and a center of rotation of each of said first and second scanning mirrors being within the focal plane of said focussing optics, but not being disposed on the optical axis of said focussing optics.

* * * * *